United States Patent [19]

Wierzbicki et al.

[11] Patent Number: 4,711,885

[45] Date of Patent: Dec. 8, 1987

[54] N-(N'-PHENYLPIPERAZINE)-ALKYL TRIAZOLE COMPOUNDS HAVING ANXIOLYTIC AND ANALGESIC PROPERTIES

[75] Inventors: Michel Wierzbicki, Puteaux; Pierre Hugon, Rueil Malmaison; Jean-Claude Poignant, Bures S/Yvette, all of France

[73] Assignee: Adir et Compagnie, Neuilly-sur-Seine, France

[21] Appl. No.: 846,911

[22] Filed: Apr. 1, 1986

[30] Foreign Application Priority Data

Apr. 17, 1985 [FR] France ................................ 85 05762

[51] Int. Cl.[4] ................. A61K 31/495; C07D 403/14; C07D 401/14
[52] U.S. Cl. ..................................... 514/253; 544/361; 544/362; 544/363; 544/366; 544/373
[58] Field of Search ............... 544/361, 362, 363, 366, 544/373; 540/476, 586, 593; 514/183, 210, 214, 215, 253

[56] References Cited

U.S. PATENT DOCUMENTS 3,381,009  4/1968  Palazzo et al. ............... 544/362
3,956,328  5/1976  Irikura ........................ 544/362
4,252,721  2/1981  Silvestrini et al. ............ 514/913

FOREIGN PATENT DOCUMENTS 206685  12/1982  Japan .......................... 544/362

Primary Examiner—Donald G. Daus
Assistant Examiner—Cecilia Shen
Attorney, Agent, or Firm—Gordon W. Hueschen

[57] ABSTRACT

Triazole compounds of the formula:

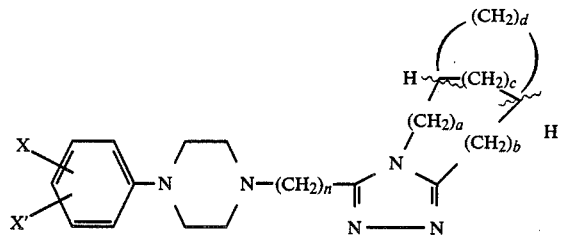

in which:
X and X', which are the same or different, each represents hydrogen, halogen, trifluoromethyl, $C_{1-5}$ alkyl, or $C_{1-5}$ alkoxy, or
X and X' together represent methylenedioxy,
n is an integer of from 1 to 6,
a is 0, 1 or 2;
b is 0, 1, 2 or 3;
c is 0, 1 or 2 and
d is 2, 3, 4 or 5 such that a+b+c+d is equal to 4, 5, 6 or 7.

These compounds and physiologically tolerable acid addition salts thereof may be used as medicines especially in the treatment of pain and anxiety.

10 Claims, No Drawings

N-(N'-PHENYLPIPERAZINE)-ALKYL TRIAZOLE COMPOUNDS HAVING ANXIOLYTIC AND ANALGESIC PROPERTIES

The present invention provides triazole compounds of the formula:

$$\text{(I)}$$

in which:
X and X', which are the same or different, are each selected from the group consisting of: a hydrogen and halogen atoms, a trifluoromethyl radical and alkyl and alkoxy radicals each having from 1 to 5 carbon atoms inclusive, and X and X' together represent a methylenedioxy radical, n is selected from the group consisting of integers of from 1 to 6, a is selected from the group consisting of the values 0, 1 and 2, b is selected from the group consisting of the values 0, 1, 2 and 3, c is selected from the group consisting of the values 0, 1 and 2, and d is selected from the group consisting of the values 2, 3, 4 and 5, such that the sum of a+b+c+d is equal to 4, 5, 6 or 7.

The state of the prior art in this field is illustrated especially by German Pat. No. 2.915.318 and Belgian Patent No. 877.161, which relate to cycloalkyl triazole derivatives of the general formula:

in which
alk represents a bivalent aliphatic chain having from 1 to 10 carbon atoms, alk' represents a linear or branched aliphatic chain having from 1 to 5 carbon atoms, and R and R' may be hydrogen, halogen, alkyl, alkoxy, hydroxy, trifluoromethyl or methylthio.

These compounds are mentioned as anti-glaucomatous and antipsychotic agents.

The introduction of a condensed alicyclic moiety in the mono-nitrogen-containing ring of these compounds resulted in the production of derivatives of the general formula I, and made it possible to demonstrate for these derivatives (I) a remarkable analgesic or anxiolytic activity not mentioned at all for the analogous compounds of the prior art.

The present invention relates also to a process for the preparation of the compounds of the general formula I characterised in that:
a compound of the general formula II $$\text{(II)}$$

in which X, X' and n have the meanings defined hereinbefore is reacted with hydrazine $H_2N-NH_2$ to obtain a compound of the general formula III $$\text{(III)}$$

in which X, X' and n are as defined hereinbefore, then, this compound (III) is reacted with a lactime ether of the general formula IV $$\text{(IV)}$$

in which a, b, c and d are as defined hereinbefore and R represents an alkyl radical having from 1 to 5 carbon atoms, preferably methyl.

The preparation of the compounds III is carried out advantageously by reacting a compound II with hydrazine hydrate in a suitably selected solvent, such as, for example, an alcohol.

The reaction of the compounds III with the lactime ethers IV is carried out especially advantageously in a suitable solvent, selected, for example, from optionally halogenated aromatic hydrocarbons, with optional distillation of the products formed (alcohols, water . . . ).

The lactime ethers of the general formula IV are themselves prepared by the action of alkylating agents, such as, for example, methyl sulfate on the corresponding lactams of the general formula IVa:

$$\text{(IVa)}$$

in which a, b, c and d are as defined hereinbefore, which lactams are products described in the literature.

The starting materials of the general formula II are themselves prepared from N-monosubstituted piperazines of the general formula IIa

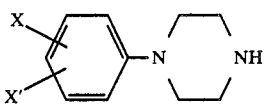 (IIa)

in which X and X' are as defined hereinbefore, which are products known from the literature, and such piperazines are reacted with a halogenated compound of the general formula IIb Hal—A—COOC₂H₅      (IIb)

in which
- Hal represents a halogen atom, such as, for example, a chlorine or bromine atom, and
- A represents a hydrocarbon chain containing n carbon atoms (n being as defined hereinbefore) and having if desired, in the case where n is greater than 1, a double bond at the position α to the ethoxycarbonyl function.

The condensation of the compounds IIa and IIb is advantageously carried out in an suitable solvent such as, for example, benzene, acetone, dimethylformamide or dioxan, optionally in the presence of a base which may be an alkaline metal hydride, an alkaline metal alchoholate or an alkaline metal carbonate, which acts as an acceptor of the hydracid formed in the course of the reaction.

This condensation is followed, in the case where A contains a double bond, by catalytic hydrogenation of the unsaturated ester so obtained.

The starting materials of the general formula II in which n is an integer of greater than 1, and which consequently correspond to the general formula II'

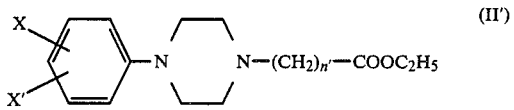 (II')

in which X and X' are as defined hereinbefore and n' represents an integer of from 2 to 6, can also be prepared by reacting N-monosubstituted piperazines of the general formula IIa, defined hereinbefore, with a compound of the general formula II'b H₂C=CH—(CH₂)ₙ'₋₂—COOC₂H₅      (II'b)

in which n' represents an integer of from 2 to 6.

The condensation is advantageously carried out in an appropriate solvent selected, for example, from alcohols and aromatic hydrocarbons.

The latter process is especially suitable for the preparation of compounds of the general formula II in which n represents 2.

The compounds (I) thus obtained can be converted into addition salts with acids, and the invention also relates to these salts. As acids that may be used for the formation of these salts, there may be mentioned, in the mineral series hydrochloric, hydrobromic, sulfuric and phosphoric acids and, in the organic series, acetic, propionic, maleic, fumaric, tartaric, citric, oxalic, benzoic and methanesulfonic acids.

The compounds of the general formula I and the physiologically tolerable salts thereof have interesting pharmacological and therapeutic properties, particularly anxiolytic or analgesic properties; consequently, they may be used as medicaments in particular in the treatment of pain and conditions of anxiety.

The present invention relates also to pharmaceutical compositions containing as active ingredient a compound of the general formula I or one of its physiologicallly tolerable salts, in admixture or association with an appropriate pharmaceutical excipient, such as, for example, distilled water, glucose, lactose, starch, talc, ethylcellulose, magnesium stearate or cacao butter.

The pharmaceutical compositions thus obtained are generally in dosage form and may contain from 3 to 300 mg of active ingredient. They may be, for example, in the form of tablets, dragées, gelatin-coated pills, suppositories, or injectable or drinkable solutions and may, depending on the case in question, be administered orally, rectally or parenterally at a dose of from 3 to 300 mg from 1 to 3 times per day.

The following Examples illustrate the invention, the melting points, unless indicated otherwise, being determined with a Kofler hot plate.

EXAMPLE 1:

8-{N'-[N-(metachlorophenyl)piperazine]-methyl}2b,3,4,5,5a,6-hexahydrotriazolo[3,4-a]cyclopenta(c)pyrrole

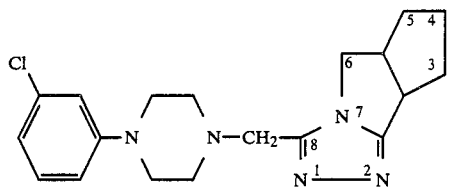

8 g of 4-(3-chlorophenyl)-piperazin-1-ylacetic acid hydrazide and 4.6 g of 2-methoxy-3-azabicyclo(3,3,0)oct-2-ene dissolved in 80 ml of xylene are heated at reflux for 20 hours, with distillation after 5, 10 and 15 hours of several milliliters in order to eliminate light products (water and methanol) formed in the reaction. The reaction mixture is then evaporated to dryness in vacuo and the residue is triturated with 100 ml of anhydrous ether. After filtration with suction the product obtained (7.6 g, m.p. 128° C.) is crystallised from 45 ml of boiling ethyl acetate. After cooling, filtration with suction, and drying, 4 g of 8-{N'-[N-(metachlorophenyl)-piperazine]-methyl}2b,3,4,5,5a,6-hexahydrotriazolo[3,4-a]cyclopenta(c)pyrrole are obtained, m.p. 155° C.

The starting materials were prepared as follows:

(A) Preparation of the hydrazide of 4-(3-chlorophenyl)-piperazin-1-ylacetic acid.

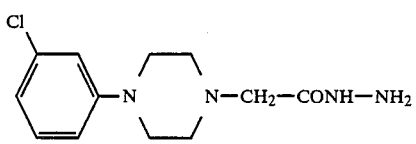

(a) 4-(3-chlorophenyl)piperazin-1-ylacetic acid ethyl ester.

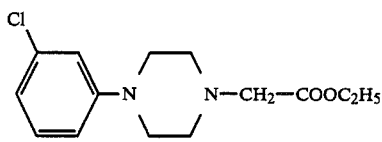

33.4 g of ethyl bromoacetate are added over a period of 20 minutes to a solution of 78.7 g of N-(3-chlorophenyl)-piperazine in 400 ml of anhydrous toluene, then the reaction mixture is maintained at reflux for 45 minutes. The hydrobromide of the title piperazine is filtered with suction and the filtrate is concentrated to dryness in vacuo. The crude product obtained is used as such in the following phase.

The following were prepared in the same manner:
4-(3-trifluoromethylphenyl)piperazin-1-ylacetic acid ethyl ester, and
4-(3,5-dichlorophenyl)piperazin-1-ylacetic acid ethyl ester.

(b) 4-(3-chlorophenyl)piperazin-1-ylacetic acid hydrazide.

56.6 g of 4-(3-chlorophenyl)-piperazin-1-ylacetic acid ethyl ester and 50 g of hydrazine hydrate are dissolved in 400 ml of ethanol. The reaction mixture is maintained at reflux for 1 hour 30 minutes. After evaporation in vacuo of the light products, the hydrazide remaining is used as such for the subsequent synthesis.

The following were prepared in the same manner:
4-(3-trifluoromethylphenyl]piperazin-1-ylacetic acid hydrazide, and
4-(3,5-dichlorophenyl)piperazin-1-yl-acetic acid hydrazide.

(B) 2-methoxy-3-azabicyclo(3,3,0)oct-2-ene:

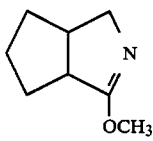

Over a period of 1 hour, 94.7 ml of dimethyl sulfate are added dropwise to a solution, maintained at reflux, of 125.2 g of 2-oxo-3-azabicyclo(3,3,0)octane in 350 ml of anhydrous benzene. Reflux is then maintained for 4 hours. After cooling, the reaction mixture is poured onto 100 ml of concentrated sodium hydroxide solution. The organic layer is decanted, and the aqueous layer is extracted twice with 200 ml of benzene each time. The benzene extracts are combined, dried over magnesium sulfate and concentrated in vacuo and the residue is distilled. In this manner 79.5 g of 2-methoxy-3-azabicyclo(3,3,0)oct-2-ene are obtained, b.p.: 64°–68° C., $n_D^{23} = 1.4718$.

The lactime ethers of the formula

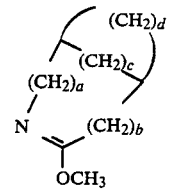

were prepared in the same manner; their characteristics are listed in the table below:

| a | b | c | d | Configuration | Physical Characteristics |
|---|---|---|---|---|---|
| 1 | 0 | 0 | 4 | — | b.p/9 mmHg = 83–85° C. $n_D^{23} = 1.4772$ |
| 1 | 1 | 0 | 4 | cis | crude product |
| 1 | 1 | 0 | 4 | trans | crude product |
| 0 | 2 | 0 | 4 | cis | crude product |
| 0 | 2 | 0 | 4 | trans | crude product |

EXAMPLE 2:

9-{β-N'-[N-(metachlorophenyl)piperazine]ethyl}-[7H]-2b,3,4,5,6,6a-hexahydrotriazolo[3,4-a]cyclohexa(c)pyrrole

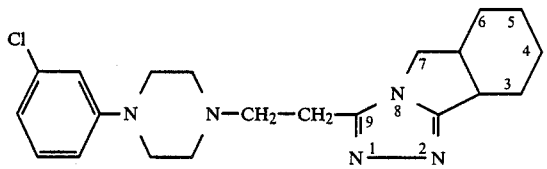

14 g of 4-(3-chlorophenyl)piperazin-1-ylpropionic acid hydrazide and 8.4 g of 2-methoxy-3-azabicyclo(4,3,0)-non-2-ene are heated for 1 hour in 120 ml of 1,2,4-trichlorobenzene. After elimination of the solvent in vacuo, the residue is recrystallised from 50 ml of ethyl acetate. 4.6 g of 9-{β-N'-[N(metachlorophenyl)-piperazine]ethyl}-[7H]-2b,3,4,5,6,6a-hexahydrotriazolo[3,4-a]cyclohexa(c)pyrrole are obtained, m.p. 152°–153° C.

The 4-(3-chlorophenyl)piperazin-1-ylpropionic acid hydrazide starting material, m.p. 113°–114° C. (acetic acid) was prepared according to the operating method described in Example 1 from 4-(3-chlorophenyl)piperazin-1-ylpropionic acid ethyl ester, itself prepared as follows:

Over a period of 40 minutes, 108 ml of ethyl acrylate are added to 38.3 g of N-(3-chlorophenyl)piperazine dissolved in 300 ml of anhydrous ethanol and 0.5 ml of Triton B. The temperature reaches 40° C. when addition is complete. After heating at reflux for 3 hours, the reaction mixture is concentrated in vacuo and the residue is distilled. 139 g of 4-(3-chlorophenyl)piperazin-1-ylpropionic acid ethyl ester are obtained, b.p/$_{0.33}$ mmHg = 176°–179° C.

The esters of the formula

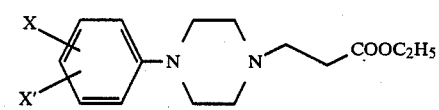

with the characteristics listed in the table below were prepared in the same manner

| X | X' | PHYSICAL CONSTANTS |
|---|---|---|
| (2)-Cl | H | b.p/0.15 mmHg = 165–166° C. |
| (4)-Cl | H | m.p.: 56–57° C. |
| (3)-CF$_3$ | H | crude liquid |
| (3)-F | H | b.p/0.1 mmHg = 155–157° C. |
| (3)-CH$_3$ | H | b.p/0.15 mmHg = 153–156° C. |
| (3)-OCH$_3$ | H | b.p/0.15 mmHg = 182–184° C. |
| (3)-Cl | (4)-Cl | crude liquid |
| (3)-Cl | (5)-Cl | m.p.: 74° C. (cyclohexane) |
| (3)-OCH$_3$ | (4)-OCH$_3$ | m.p.: 48° C. |
| (3)-CF$_3$ | (4)-Cl | b.p/0.4 mmHg 162–168° C. |
| (3)-CF$_3$ | (4)-F | b.p/0.3 mmHg = 156° C. |
| (3,4)-O—CH$_2$—O— | | m.p.: 50° C. |

There were prepared from these esters the corresponding hydrazides of the formula

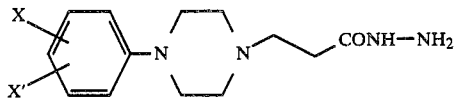

the characteristics of which are listed in the following Table:

| X | X' | PHYSICAL CONSTANTS |
|---|---|---|
| (2)-Cl | H | m.p.: 132–133° C. (isopropanol) |
| (4)-Cl | H | m.p.: 154° C. (isopropanol) |
| (3)-CF$_3$ | H | m.p.: 99° C. (C$_6$H$_6$/petroleum ether) |
| (3)-F | H | m.p.: 130° C. (isopropanol) |
| (3)-CH$_3$ | H | m.p.: 98° C. (isopropanol) |
| (3)-Cl | (4)-Cl | m.p.: 88–90° C. (benzene) |
| (3)-Cl | (5)-Cl | m.p.: 136° C. (isopropanol) |
| (3)-CF$_3$ | (4)-Cl | crude liquid |
| (3)-CF$_3$ | (4)-F | m.p.: 96° C. (CH$_3$COOH/petroleum ether) |
| (3)-OCH$_3$ | H | m.p.: 121–122° C. (isopropanol) |
| (3)-OCH$_3$ | (4)-OCH$_3$ | m.p.: 142° C. (isopropanol) |
| (3,4)-O—CH$_2$—O— | | m.p.: 142° C. (isopropanol) |

EXAMPLE 3:

Cis-10-{γ-N-[N'(metatrifluoromethylphenyl)-piperazine]n-propyl}-3,3a,4,5,6,7,7a,8-octahydrotriazolo[4,3-b]isoquinoline.

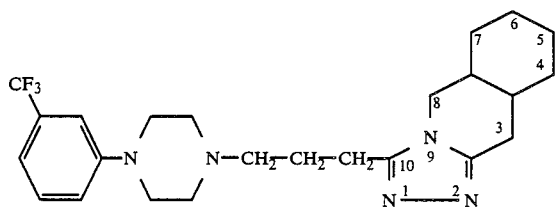

11 g of 4-(3-trifluoromethylphenyl)piperazin-1-ylbutanoic acid hydrazide and 7.5 g of 4-methoxy-3-azabicyclo(4,4,0)dec-3-ene (cis form) in 75 ml of xylene is used as starting material and, by operating as in Example 1, then treating the residue, after elimination of the solvent, with 100 ml of anhydrous isopropanol and 27 ml of a 2.44N saturated solution of hydrogen chloride in ethyl ether. 4.7 g of cis-10-{γ-N-[N'-(metatrifluoromethylphenyl)piperazine]-n.propyl}-3,3a,4,5,6,7,7a,8-octahydrotriazolo[4,3-b]isoquinoline dihydrochloride are obtained, m.p. 210°–220° C. (isopropanol).

The 4-(3-trifluoromethylphenyl)piperazin-1-ylbutanoic acid hydrazide used as starting material was prepared by operating as in Example 1, from 4-(3-trifluoromethylphenyl)piperazin-1-ylbutanoic acid ethyl ester, itself prepared as follows:

Over a period of 20 minutes 29 g of ethyl 4-bromocrotonate are added to 69 g of 1-(3-trifluoromethylphenyl)-piperazine dissolved in 300 ml of anhydrous toluene. The mixture is then heated at reflux for 1 hour. After cooling, the hydrobromide is filtered with suction and the filtrate is concentrate to dryness in vacuo. In this manner crude 4-(3-trifluoromethylphenyl)piperazin-1-ylbut-2-enoic acid ethyl ester is obtained in theoretical yield.

23 g of this ester dissolved in 200 ml of ethanol are hydrogenated under 60 lbs of pressure in the presence of Raney nickel. The theoretical quantity of hydrogen is absorbed in 3 hours. After filtration of the catalyst, the filtrate is concentrated in vacuo and the residue is distilled. In this manner 31 g of 4-(3-trifluoromethylphenyl)piperazin-1-ylbutanoic acid ethyl ester are obtained, b.p.$_{0.3\ mm\ Hg}$=146°–147° C.

In the same manner 4-(3-chlorophenyl)piperazin-1-ylbutanoic acid ethyl ester and 4-(3,5-dichlorophenyl)-piperazin-1-ylbutanoic acid ethyl ester were prepared, each of which is a liquid obtained and used in the crude state for the preparation of, respectively: 4-(3-chlorophenyl)piperazin-1-ylbutanoic acid hydrazide, m.p. 45°–50° C. (ether) and 4-(3,5-dichlorophenyl)piperazin-1-yl)butanoic acid hydrazide, m.p. 136° C. (isopropanol).

EXAMPLES 4–56:

By proceeding as in the aforegoing Examples, the products with the characteristics listed in the Table below were prepared:

Formula:

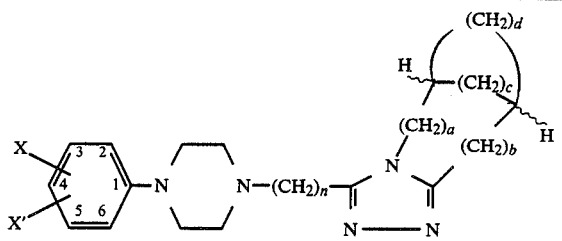

| EX | X | X' | n | a | b | c | d | RING JUNCTION | PHYSICAL CONSTANTS |
|---|---|---|---|---|---|---|---|---|---|
| 4 | (3)CF$_3$ | H | 1 | 1 | 1 | 0 | 4 | trans | m.p.: 143° C. base |
| 5 | (3)Cl | H | 1 | 0 | 2 | 0 | 4 | trans | m.p.: 161–162° C. base |
| 6 | (3)Cl | H | 1 | 2 | 0 | 0 | 4 | cis | m.p.: 174° C. base |
| 7 | (3)Cl | H | 1 | 0 | 2 | 0 | 4 | cis | m.p.: 173–174° C. base |
| 8 | (3)CF$_3$ | H | 1 | 1 | 0 | 0 | 3 | | m.p.: 128° C. base |
| 9 | (3)Cl | (5)Cl | 1 | 0 | 2 | 0 | 4 | cis | m.p.: 166–167° C. base |
| 10 | (3)Cl | (5)Cl | 1 | 0 | 2 | 0 | 4 | trans | m.p.: 180° C. base |
| 11 | (3)Cl | H | 2 | 1 | 1 | 0 | 4 | cis | m.p.: 130° C. base |
| 12 | (3)Cl | H | 2 | 0 | 2 | 0 | 4 | trans | m.p.: 162° C. base |
| 13 | (3)Cl | H | 2 | 1 | 0 | 0 | 3 | | m.p.: 156° C. base |
| 14 | (3)Cl | H | 2 | 1 | 1 | 0 | 4 | trans | m.p.: 132° C. base |
| 15 | (3)CF$_3$ | H | 2 | 0 | 2 | 0 | 4 | trans | m.p.: 152° C. base |
| 16 | (3)CF$_3$ | H | 2 | 1 | 1 | 0 | 4 | cis | m.p.: 144° C. base |
| 17a | (3)CF$_3$ | H | 2 | 1 | 0 | 0 | 3 | | m.p.: 138° C. base |
| 17b | (3)CF$_3$ | H | 2 | 1 | 0 | 0 | 3 | | m.p.: 168° C. base methane sulfonate |
| 17c | (3)CF$_3$ | H | 2 | 1 | 0 | 0 | 3 | | m.p.: 262° C. (dec) monohydrochloride |
| 17d | (3)CF$_3$ | H | 2 | 1 | 0 | 0 | 3 | | m.p.: 240° C. dihydrochloride |
| 18 | (3)Cl | H | 2 | 2 | 0 | 0 | 4 | cis | m.p.: 183–184° C. base |
| 19 | (3)CF$_3$ | H | 2 | 2 | 0 | 0 | 4 | cis | m.p.: 176° C. base |
| 20 | (3)Cl | H | 2 | 0 | 0 | 2 | 2 | | m.p.: 116° C. base |
| 21 | (3)CF$_3$ | H | 2 | 0 | 0 | 2 | 2 | | m.p.: 136° C. base |
| 22 | (3)OCH$_3$ | H | 2 | 0 | 2 | 0 | 4 | trans | m.p.: 137–138° C. base |
| 23 | (3)CF$_3$ | (4)F | 2 | 0 | 2 | 0 | 4 | trans | m.p.: 185° C. base |
| 24 | (3)OCH$_3$ | (4)OCH$_3$ | 2 | 0 | 2 | 0 | 4 | trans | m.p.: 145° C. base |
| 25 | (4)Cl | H | 2 | 0 | 2 | 0 | 4 | trans | m.p.: 170–171° C. base |
| 26 | (3)F | H | 2 | 0 | 2 | 0 | 4 | trans | m.p.: 135–136° C. base |
| 27 | (3)CF$_3$ | (4)Cl | 2 | 0 | 2 | 0 | 4 | trans | m.p.: 180° C. base |
| 28 | (3)Cl | (5)Cl | 2 | 0 | 2 | 0 | 4 | trans | m.p.: 176° C. base |
| 29 | (3)CH$_3$ | H | 2 | 0 | 2 | 0 | 4 | trans | m.p.: 146° C. base |
| 30 | (2)Cl | H | 2 | 0 | 2 | 0 | 4 | trans | m.p.: 157–158° C. base |
| 31 | (3)Cl | (4)Cl | 2 | 0 | 2 | 0 | 4 | trans | m.p.: 192° C. base |
| 32 | (3,4)-O—CH$_2$—O | | 2 | 0 | 2 | 0 | 4 | trans | m.p.: 125° C. base |
| 33 | (3)CF$_3$ | (4)Cl | 2 | 0 | 2 | 0 | 4 | cis | m.p.: 173° C. base |
| 34 | (3)Cl | H | 2 | 0 | 2 | 0 | 4 | cis | m.p.: 145–146° C. base |
| 35 | (3)OCH$_3$ | (4)OCH$_3$ | 2 | 0 | 2 | 0 | 4 | cis | m.p.: 135° C. base |
| 36 | (3)CF$_3$ | H | 2 | 1 | 0 | 0 | 4 | | m.p.: 140° C. base |
| 37 | (3)Cl | (5)Cl | 2 | 0 | 2 | 0 | 4 | cis | m.p.: 215–232° C. base dihydrochloride |
| 38 | (3)Cl | (5)Cl | 2 | 1 | 0 | 0 | 3 | | m.p. >260° C. base dihydrochloride |
| 39 | (3)Cl | (5)Cl | 2 | 1 | 1 | 0 | 4 | cis | m.p.: 162–164° C. base |
| 40 | (3)Cl | H | 3 | 1 | 1 | 0 | 4 | cis | m.p. >260° C. dihydrochloride |
| 41 | (3)Cl | (5)Cl | 3 | 0 | 2 | 0 | 4 | trans | m.p.: 149° C. base |
| 42 | (3)Cl | H | 3 | 0 | 2 | 0 | 4 | cis | m.p.: 210–215° C. dihydrochloride |
| 43 | (3)Cl | (5)Cl | 3 | 0 | 2 | 0 | 4 | cis | m.p.: 137° C. base |
| 44 | (4)CF$_3$ | H | 3 | 1 | 1 | 0 | 4 | cis | m.p.: 250–255° C. dihydrochloride |
| 45 | (3)CF$_3$ | H | 3 | 1 | 0 | 0 | 3 | | m.p.: 230° C. trihydrochloride |
| 46 | (3)CF$_3$ | H | 3 | 0 | 2 | 0 | 4 | trans | m.p.: 210–212° C. dihydrochloride |
| 47 | (2)CF$_3$ | H | 3 | 1 | 1 | 0 | 4 | cis | m.p.: 242–246° C. dihydrochloride |
| 48 | (3)Cl | H | 3 | 0 | 2 | 0 | 5 | cis | m.p.: 228–230° C. dihydrochloride |
| 49 | (3)Cl | H | 4 | 1 | 1 | 0 | 4 | cis | m.p.: 120–121° C. base |
| 50 | (3)CF$_3$ | H | 4 | 1 | 1 | 0 | 4 | cis | m.p.: 112–114° C. base |
| 51 | (3)Cl | H | 4 | 1 | 0 | 0 | 3 | | m.p.: 129° C. base |
| 52 | (3)CF$_3$ | H | 4 | 1 | 0 | 0 | 3 | | m.p.: 109° C. base |
| 53 | (3)Cl | H | 5 | 1 | 1 | 0 | 4 | cis | m.p.: 230–232° C. dihydrochloride |
| 54 | (3)CF$_3$ | H | 5 | 1 | 1 | 0 | 4 | cis | m.p.: 220° C. |

-continued

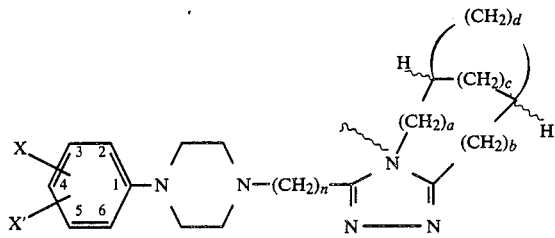

| EX | X | X' | n | a | b | c | d | RING JUNCTION | PHYSICAL CONSTANTS |
|---|---|---|---|---|---|---|---|---|---|
| 55 | (3)Cl | H | 5 | 0 | 2 | 0 | 5 | cis | dihydrochloride m.p.: 198–200° C. |
| 56 | (3)CF$_3$ | H | 5 | 0 | 2 | 0 | 5 | cis | dihydrochloride m.p.: 180–185° C. dihydrochloride |

PHARMACOLOGICAL STUDY OF THE COMPOUNDS OF THE PRESENT INVENTION

The analgesic activity of the compounds of the present invention was studied by means of the tail-flick test according to D'Amour F. E. and Smith D. L., Journal of pharmacology and experimental therapeutics, 72, 74–79 (1941), the hot plate test according to Woolfe G. and MacDonald A. D., Journal of pharmacology and experimental therapeutics, 80, 300–307 (1944) and the phenylbenzoquinone test according to Siegmund E., Cadmus R. and Lu G, Proc. Soc. Exptle. Biol. Med. 95, 729–731 (1957).

The anxiolytic activity was studied, for its part, by means of the four plates test according to Aron C., Simon P., Larousse C. and Boissier J. R., Neuropharmacology, 10, 459–469, (1971), the conflict test according to Vogel J. R., Beer B., Clody D. E., Physchopharmacol. 21, 1–7, (1971) and the punishment test according to Mac Millan D. E., J. Exp. Anal. Behav, 19, 133–145 (1973).

By way of example, the following table lists the results of the analgesic effects observed in mice for several representative products of the invention:

| Compounds of Examples No. | Siegmund Test ED$_{50}$ mg/kg p.o. | Hot Plate Test ED$_{50}$ mg/kg i.p. | Tail-Flick Test ED$_{50}$ mg/kg i.p. |
|---|---|---|---|
| 2 | 8.7 | >50 | >50 |
| 3 | 16.0 | 19.8 | >50 |
| 12 | 25.7 | 25.3 | 30.7 |
| 16 | 17.0 | 24.3 | >50 |
| 17a | 5.82 | 21.3 | >50 |
| 36 | 4.3 | 25 < ED$_{50}$ < 50 | >50 |
| 40 | 7.5 | 53.9 | >50 |
| 42 | 11.4 | >50 | >50 |

Note: The mean effective dose (ED$_{50}$) was calculated:
in the Siegmund test from the percentage variations in the number of contractions of the abdomen compared with the control batch;
in the hot plate test from the percentage variation in the licking time (in seconds) compared with the control batch.
in the tail-flick test from the percentage variations in the reaction time (in seconds) by comparison with the control batch.

The compounds of Examples 2, 36 and 40 have a very significant analgesic activiy in the Siegmund test. In the tail-flick test no compound is active at a dose of 50 mg/kg i.p. with the exception of the compound of Example 12.

In the hot plate test, the compounds have a mild analgesic activity since the ED$_{50}$ values calculated are generally between 20 and 50 mg/kg i.p., which shows that, for the derivatives of the invention, the activity on the C N S level of the analgesic effects observed is weak.

The anxiolytic effects of the compounds of the invention are illustrated by the results listed in the following tables:

| | 4 PLATES TEST (MICE) | | | |
|---|---|---|---|---|
| | % NUMBER OF SHOCKS RECEIVED (N = 10) | | | |
| Compound of | Dose mg/kg i.p. | | | |
| Example No. | 2.5 | 5 | 10 | 25 |
| Compound of | | | | |
| 3 | +38% S | +44% S | +48% S | 18% |
| 12 | +38% S | +15% | +20% | +2% |
| 16 | −12% | +2% | +32% S | +5% |
| 17a | +18% | +26% S | +35% S | +61% S |
| 17b | +15% | +34% S | +53% S | +27% |
| 36 | −12% | −4% | −4% | +39% S |

S = Significant (p < 0.05) modification of shocks received.

| MAC-MILLAN TEST PUNISHMENT OPERATING CONDITIONING (RATS) PERCENTAGE VARIATION IN THE NUMBER OF PUNISHED RESPONSES (N ≧ 9) (N = Number of animals) | | | | |
|---|---|---|---|---|
| Compound of | Dose mg/kg i.p. | | | |
| Example No. | 2.5 | 5 | 10 | 20 |
| 12 | −33.5% | −24% S | −51.3% | −75% S |
| 16 | +5.4% | +42.2% | +125.9% S | −60.7% S |
| 17a | +47.8% S | +33.6% S | +42.6% | −70.3% S |

S = Significant modification

In the 4 plates test, the compounds of Examples 3, 12, 16, 17a, 17b and 36 provide results in favour of a very significant anxiolytic activity. The same is true of the compounds of Examples 16 and 17a in the conflict test according to MacMillan.

The conclusion that may be drawn is one of a very interesting therapeutic use of the products of the invention in the treatment of conditions of anxiety of endogenous origin.

We claim:

1. A compound selected from the group consisting of: triazole compounds of the formula:

$$\begin{array}{c}\text{X}\underset{\text{X}'}{\diagdown}\!\!\!\!\!\!-\!\!\!\!\bigcirc\!\!-N\diagdown\!\!\!\!\!\!\!\!\!\!\!\diagup\!\!\!N-(CH_2)_n-\overset{(CH_2)_d}{\underset{N-\!\!\!-N}{\overset{H\diagdown}{\diagup}}\overset{(CH_2)_c}{\underset{(CH_2)_a}{\diagdown}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!}\end{array} \quad (I)$$

in which:

X and X', which are the same or different, are each selected from the group consisting of hydrogen, halogen, trifluoromethyl, and alkyl and alkoxy each having from 1 to 5 carbon atoms inclusive, and X and X' together represent methylenedioxy, n is selected from the group consisting of integers of from 1 to 6, a is selected from the group consisting of 0, 1 and 2, b is selected from the group consisting of 0, 1, 2 and 3, c is selected from the group consisting of 0, 1 and 2, and d is selected from the group consisting of 2, 3, 4 and 5 such that the sum of $a+b+c+d$ is equal to 4, 5, 6 or 7, and physiologically tolerable acid addition salts thereof.

2. A compound of claim 1 which is:
9-{β-N'-[N-(metachlorophenyl)piperazine]ethyl}-[7H]-2b,3,4,5,6,6a-hexahydrotriazolo[3,4-a]isoindole.

3. A compound of claim 1 which is:
Cis-10-{-N-[N'-(metatrifluoromethylphenyl)-piperazine]n.propyl}-3,3a,4,5,6,7,7a,8-octahydro-triazolo-[4,3-b]isoquinoline.

4. A compound of claim 1 which is:
Trans-10{β-N-[N'-(metachlorophenyl)piperazine]-ethyl}-3,4,4a,5,6,7,8,8a-octahydrotriazolo[4,3-a]-quinoline.

5. A compound of claim 1 which is:
Cis-10-{β-N-[N'-(metatrifluoromethylphenyl)-piperazine]ethyl}-3,3a,4,5,6,7,7a,8-octahydro-triazolo[4,3-b]isoquinoline.

6. Compounds of claim 1 which are:
8-{β-N-[N'-(metatrifluoromethylphenyl)-piperazine]ethyl}-[6H]-2b,5a-dihydrotriazolo[3,4-a]cyclopenta (c) pyrrole, and methane sulfonate, monohydrochloride and dihydrochloride thereof.

7. A compound of claim 1 which is:
9-}β-N[N'-(metatrifluoromethylphenyl)piperazine]e-thyl}-[7H]-2b,3,4,5,6,6a-hexahydrotriazolo[3,4-a]isoindole.

8. A compound of claim 1 which is:
Cis-10{γ-N-[N'-(metachlorophenyl)piperazine]-n.propyl}-3,3a,4,5,6,7,7a,8-octahydrotriazolo[4,3-b]-isoquinoline.

9. Pharmaceutical composition suitable for use in the alleviation of pain or anxiety containing as active ingredient an effective pain- or anxiety-relieving amount of a compound of claim 1 together with a suitable pharmaceutical carrier.

10. A method for treating a living animal body afflicted with pain or anxiety comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,711,885
DATED : December 8, 1987
INVENTOR(S) : Michel Wierzbicki, Pierre Hugon and Jean-Claude Poignant It is certified that error appears in the above-identified patent and that said Letters Patent is hereby corrected as shown below:

Col. 1, line 22; delete "a"
Col. 3, line 23; "an" should read -- a --
Col. 3, line 27; "alchoholate" should read -- alcoholate --
Col. 4, lines 5&6; "physiologicallly" should read -- physiologically --
Col. 7 approximately line 16, (in the first table, last column, line 10 under the heading of "PHYSICAL CONSTANTS"); "mmHg 162-" should read -- mmHg = 162- --
Col. 8, line 31; "concentrate" should read -- concentrated --
Cols. 9&10, in the table, last column under "PHYSICAL CONSTANTS", line 15; delete "base"
Col. 11, in the first table "-continued", the formula has a squiggly line coming from the "N"; delete that line
Col. 11, line 62; "activiy" should read -- activity --
Col. 12, line 36, (in the table, directly below "Compound of Example No."); delete the repeated "Compound of"
Col. 12, line 38, (in the table, fourth column) after "+20%" delete that arc-shaped line
Col. 14, line 18; "9-⟩β-" should read -- 9-⟩β- --

Signed and Sealed this

Twelfth Day of July, 1988

*Attest:*

*Attesting Officer*

DONALD J. QUIGG

*Commissioner of Patents and Trademarks*